(12) United States Patent
Berger

(10) Patent No.: US 8,374,697 B2
(45) Date of Patent: Feb. 12, 2013

(54) ELECTRICAL DENTAL SCREW IMPLANT

(76) Inventor: J. Lee Berger, Franklin Lakes, NJ (US)

( * ) Notice: Subject to any disclaimer, the term of this patent is extended or adjusted under 35 U.S.C. 154(b) by 409 days.

(21) Appl. No.: 12/656,615

(22) Filed: Feb. 4, 2010

(65) Prior Publication Data
US 2010/0143871 A1 Jun. 10, 2010

Related U.S. Application Data

(63) Continuation-in-part of application No. 12/071,412, filed on Feb. 21, 2008, now abandoned.

(60) Provisional application No. 60/907,622, filed on Apr. 11, 2007.

(51) Int. Cl.
*A61N 1/05* (2006.01)

(52) U.S. Cl. .............................. 607/51; 607/43; 607/50

(58) Field of Classification Search .................... 607/50, 607/51, 43
See application file for complete search history.

(56) References Cited

U.S. PATENT DOCUMENTS

| | | | |
|---|---|---|---|
| 4,027,392 A | 6/1977 | Sawyer et al. | |
| 4,175,565 A * | 11/1979 | Chiarenza et al. | ............. 433/32 |
| 5,030,236 A | 7/1991 | Dean | |
| 5,292,252 A | 3/1994 | Nickerson et al. | |
| 5,607,426 A | 3/1997 | Ralph et al. | |
| 5,738,521 A | 4/1998 | Dugot | |
| 6,034,295 A | 3/2000 | Rehberg et al. | |
| 6,120,502 A * | 9/2000 | Michelson | ................... 606/247 |
| 6,605,089 B1 | 8/2003 | Michelson | |
| 2004/0243207 A1* | 12/2004 | Olson et al. | ................... 607/116 |
| 2006/0276870 A1* | 12/2006 | McGinnis | ..................... 607/145 |

OTHER PUBLICATIONS

I. Yasuda, "Fundamental aspects of fracture treatement", J. Kyoto Med. Assoc. 4: 395-406, 1953, reprinted in Clin Orthop Relat Res., (124):5-8, May 1977.
K.S. McLeod, C.T. Rubin, "The effect of low frequency electrical fields on osteogenesis", J. Bone Joint Surg. 74a:920-929, 1992.
E. Fukada, I. Yasuda, "On the piezoelectric effect of bone", J. Physiol. Soc. Jpn., 12:1158-62, Oct. 1957.
Fitzsimmons et al., "Frequency dependence of increased cell proliferation" etc., J. Cell Physiol. 139:589-591, 1989.

* cited by examiner

*Primary Examiner* — Carl H Layno
*Assistant Examiner* — Natasha Patel
(74) *Attorney, Agent, or Firm* — John S. Hale; Gipple & Hale

(57) ABSTRACT

Stimulation of bone growth to facilitate healing of a dental implant utilizing a interiorly threaded dental screw of non-conductive material in conjunction with a healing cap abutment whereby electrical stimulation facilitates healing of the surgical site. The device is powered by a battery for the purpose of creating an electrical-magnetic field to promote bone healing and bone formation. The electric magnetic field is directed to the bone around the device through a battery of a rechargeable type. A constant current is generated in a preferred range of about 5 µA to about 20 µA to stimulate bone healing and bone formation.

19 Claims, 6 Drawing Sheets

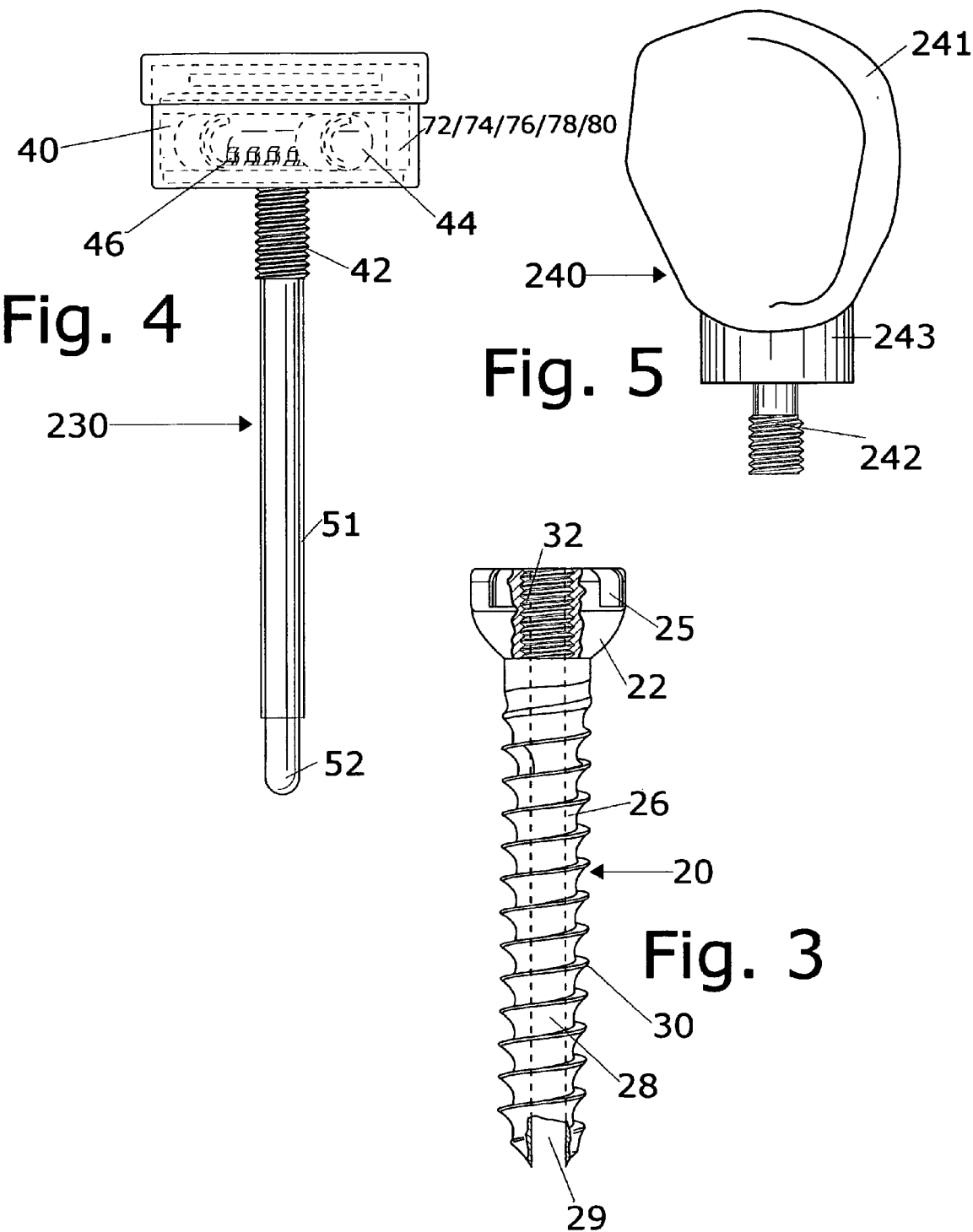

ELECTRICAL DENTAL SCREW IMPLANT

RELATED APPLICATIONS

This application is a Continuation-In-Part of U.S. patent application Ser. No. 12/071,412, now published as U.S. Patent Publication No. 2008/0255556, filed Feb. 21, 2008, now abandoned which claims priority from U.S. Provisional Application No. 60/907,622 filed Apr. 11, 2007, and the disclosures therein are incorporated herein by reference.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISC APPENDIX

None.

FIELD OF THE INVENTION

The present invention is generally directed toward a dental implant having osteogenic properties, and more specifically to a threaded screw-type implant made of nonconductive material in combination with a hermetically sealed healing cap abutment which houses its electrical elements and power source. The abutment is optionally formed to simulate the appearance of dentition and is mounted to provide electrical stimulation for bone growth.

BACKGROUND OF THE INVENTION

The implantation of prosthetic teeth to replace those lost to trauma or natural causes dates to at least the pre-Columbian era in the Americas wherein excavation of a Mayan burial site has identified skeletons with shells integrated into the mandible. More recent history, however, dates to approximately 1965 during which an experimental subject was implanted with a screw-like titanium device that in time became incorporated into the subject's bone.

Currently, the majority of dental implants are shaped like small, self-tapping screws, with either tapered or parallel sides. While those skilled in the art will understand that while a significant amount of preparation and skill is required in order to perform the procedure successfully, the procedure is conceptually simple. The orthodontic surgeon extracts the damaged tooth, screws in the implant, and after sufficient time has passed to allow the surgical site to heal and for bone to grow into and around the implant, a prosthetic tooth is threaded into the implant. Alternatively, in cases where the tooth and its root have been gone for a sufficiently long period of time such that the hole where the tooth root had been has filled with bone, a hole must first be drilled prior to carrying on the operations detailed above. Finally, where entire sections of dentition must be replaced, the orthodontic surgeon may instead opt to use an implant supported fixed bridge whereby multiple implants are emplaced in order to anchor dental bridgework.

Complications with this procedure arise, however, due to the two to six months required for osteogenesis and osteointegration (i.e., the bone in growth described above) to occur. During this healing period, the implant cannot withstand the impacts resulting from ordinary life, for example mastication or night-time tooth grinding. Hence, various protective strategies have been employed to ensure proper healing. Most commonly, a cover screw is threaded into the same hole which is later used for attaching the prosthetic tooth such that its head lies at or below the gum line so that the surrounding intact teeth will tend to protect the surgical site from impact. Unfortunately, all such methods are uncomfortable, and even painful to the patient. Perhaps more importantly, these methods generally cannot prevent movement of the implant during the up to six month healing process resulting in misalignment of the prosthesis potentially requiring reparative surgery. Therefore, there is a need for a way to speed healing, including osteogenesis and osteointegration.

The present invention is directed toward the electronic stimulation of bone to promote bone growth (osteogenesis) through or around a dental implant device in conjunction with an attached healing cap abutment functioning as a bone growth stimulator. In a technique similar to traditional dental implant procedures, the implant is first inserted into bone with or without a supplemental bone graft, or utilizing BMP, OPI, or other bone growth material including cement, biologicals, ceramics, glass, and the like. Thereafter, the bone growth stimulator of the present invention is attached to the dental screw implant whereupon the dental implant is activated by creating an electrical field around the entire screw and the surrounding tissues to promote osteogenesis of new bone and osteointegration as new bone growth forms into the surface of the implant. The device generates current ranging from about 5 $\mu$A to 50 $\mu$A to stimulate bone formation thereby reducing the healing time required before attachment of prosthetic dentition. After a period of time sufficient to ensure bone formation and osteointegration of the implant via, for example, a radiological study, a traditional dental crown or tooth is attached to the implant in lieu of the bone growth stimulator. In addition, it is contemplated that a "smart" tooth containing RFID technology and/or biological sensors may also be incorporated into the device.

It has long been known that the application of electric currents (electrical stimulation) can speed bone growth and healing. The present invention utilizes this phenomenon in a screw-type dental implant and bone growth stimulator for uses including expediting osteointegration and facilitating healing of the surgical site. Use of electrical current to stimulate bone growth has been known in the treatment of fractures, nonunion of bone and to hasten rates of bone fusion since at least the 1800s. Yasuda, in Japan in the 1950s, studied the effect of electricity in the treatment of fractures. E. Fukuda in "On the piezoelectric effect of bone", J Physiol. Soc. Jpn. 12:1158-62, 1957, and Yasuda, J. Kyoto Med. Assoc. 4: 395-406, 1953 showed that electric signals could enhance fracture healing. Both direct current capacitative coupled electric fields and alternately pulsed electromagnetic fields affect bone cell activity in living bone tissue.

Bone has bioelectrical properties generated by naturally occurring stress potentials. When the bone is stressed, it will carry an electropositive charge on the convex side and an electronegative charge on the concave side. Accordingly, Wolff's Law dictates that bone will form new bone in areas of compression and will be resorbed in areas of tension. This biological response to stress in bone creates mechanically generated electrical fields or "strain related potentials." Areas of active growth in bones carry an electronegative charge. When a bone fractures, the bone becomes electronegative at the fracture site. At the cellular level, it has been shown that osteoblasts are activated by electronegative charges. Research on the effects of electrical forces on bone cells with regard to bone formation and healing has demonstrated that bone healing can be hastened and enhanced by electricity.

Studies have shown that by implanting an electrical stimulation device and applying an electrical current around the bone, bone formation is increased around the cathode (negative electrode) and decreased around the anode (positive electrode). Further research of the use of bone growth stimulators has shown that the optimal current for bone growth with electrical stimulation is between 5 and 20 μA.

K. S. McLeod and C. T. Rubin in "The effect of low frequency electrical fields on osteogenesis", J. Bone Joint Surg. 74a:920-929, 1992, used varying sinusoidal fields to stimulate bone remodeling. These authors determined that extremely low frequency sinusoidal electric fields (smaller than 150 Hz) were effective in preventing bone loss and inducing bone formation. They also found strong frequency selectivity in the range of 15-30 Hz. Fitzsimmons et al. in "Frequency dependence of increased cell proliferation", J Cell Physiol. 139(3):586-91, 1985, found a frequency specific increase in osteogenic cell proliferation at 14-16 Hz.

U.S. Pat. No. 5,292,252 issued Mar. 8, 1994 discloses a stimulator healing cap powered by a small internal battery. The cap can be reversibly attached to a dental implant, and stimulates bone growth and tissue healing by application of a direct current path or electromagnetic field in the vicinity of bone tissue surrounding the implant, after the implant is surgically inserted. Its implant, however, uses a traditional electrically conductive "titanium or titanium alloy" material such that particular attention must be paid to ensuring the device is not electrically shorted. Moreover, the design of the device is such that electrical stimulation is directed at the cortical bone at the surface of the mandible rather than the cancellous tissue where osteointegration primarily occurs.

Another dental device described in U.S. Pat. No. 4,027,392 issued Jun. 7, 1972 discloses an embodiment of a bionic tooth powered by a battery including an AC circuit. The microcircuitry indicated by its FIG. 3 is not shown as being incorporated within the cap. While its "battery 36" can be withdrawn once healing has been completed, most of the circuitry and associated electronics remains embedded in the patient, with the attendant increases risk of microbial infiltration therein and infection. Moreover, this device suffers from the same disadvantage as the '252 patent as stimulation is directed at the cortical layer of bone rather than at the cancellous tissues where the majority of the anchor body is located and electrical stimulation would be most effective.

Yet another related device is disclosed by in U.S. Pat. No. 5,738,521 issued Apr. 14, 1998 which describes a method for accelerating osteointegration of metal bone implants using AC electrical stimulation, with a preferably symmetrical 20 μA rms, 60 kHz alternating current signal powered by a small 1.5 V battery. This system is not a compact, self-powered stimulator cap, but is externally wired and powered.

Osteogenic devices are described in U.S. Pat. No. 6,605,089 issued Aug. 12, 2003 which discloses a self contained implant having a surgically implantable, renewable power supply and related control circuitry for delivering electrical current directly to an implant which is surgically implanted within the intervertebral space between two adjacent vertebrae. Electrical current is delivered directly to the implant and thus directly to the area in which the promotion of bone growth is desired.

U.S. Pat. No. 6,034,295 issued Mar. 7, 2000 discloses an implantable device with a biocompatible body having at least one interior cavity that communicates through at least one opening with the surrounding body so that tissue surrounding the implantable device can grow through the opening. Two or more electrodes are contained within the device having terminals for supplying a low-frequency electrical alternating voltage and at least one of which is located inside the cavity. U.S. Pat. No. 5,030,236 issued Jul. 9, 1991 discloses the use of electrical energy that relies upon radio frequency energy coupled inductively into an implanted coil to provide therapeutic energy. However, none of these devices perform satisfactory osteogenesis promotion, while leaving the implant member or stem essentially unchanged in appearance and mechanical properties.

The art that relates specifically to bone growth stimulation by small, self powered electrical means is very limited and most of the bone graft stimulation has been undertaken using power sources located outside the patient's body because of the problem that when the implant is self powered, the power short circuits against the metal screw or device.

Accordingly, the present invention is a self-powered osteogenesis-inducing dental screw-type implant that can generate electrical stimulation signals when used in conjunction with its

SUMMARY OF THE INVENTION

According to the present invention there is provided an osteogenesis-inducing dental screw implant that can generate electrical stimulation signals, including a dental implant member in the nature of a nonconductive screw and a cover screw member having a battery cap mounted thereto to provide electrical signals from the cap to the tip of the screw to function as an electrical bone growth stimulation device.

It is still another object of the invention to provide a self container power source and generating circuit in the dental implant.

It is yet another object of the invention to provide a powered electrical dental screw implant which does not short out when used for electrical stimulation of bone.

It is another object of the present invention to provide an electrical dental screw bone growth promotion implant in which an active cathode is fully contained within the osteogenesis-inducing mass.

It is a further object of the invention to provide a method of fixation of dental implants that enhances bone healing with the use of electricity that can be applied through or around the implant.

It is yet another object of the invention to provide a dental screw implant to which a bone growth stimulator can be attached to enhance bone formation.

It is still another object of the invention to provide a self powered dental screw implant with a tissue-contacting body having an external surface in contact with biological tissue and having a hollow enclosure, a conductive element in electrical communication with the hollow enclosure and electrically isolated from the external surface, and an electrical stimulation mechanism located within the hollow enclosure for providing electrical stimulation to the biological tissue through the conductive element.

It is yet another object of the present invention to provide an electrical bone growth promotion dental screw implant in which the power source can be wholly or partially supplied or recharged by externally applied sources;

It is still another object of the invention to provide an implantable bone growth stimulator that can provide a D.C., constant current source;

It is yet a further object of the present invention to provide an implantable bone growth stimulator that can be attached to a dental screw implant in combination with an internal or external implantable cathode and anode; and, It is another object of the present invention to provide an implantable bone growth stimulator and dental screw implant to which a radio frequency identification device can be embedded or attached.

These and other objects, advantages, and novel features of the present invention will become apparent when considered with the teachings contained in the detailed disclosure along with the accompanying drawings.

BRIEF DESCRIPTION OF THE DRAWINGS

FIG. 3 is a partial cutaway of the interiorly threaded dental screw of the present invention showing its through going lumen in phantom;

FIG. 4 shows the bone growth stimulator of the present invention with internal electrical elements in phantom;

FIG. 5 shows prosthetic tooth of the present invention;

DETAILED DESCRIPTION OF THE INVENTION

Figure 1:
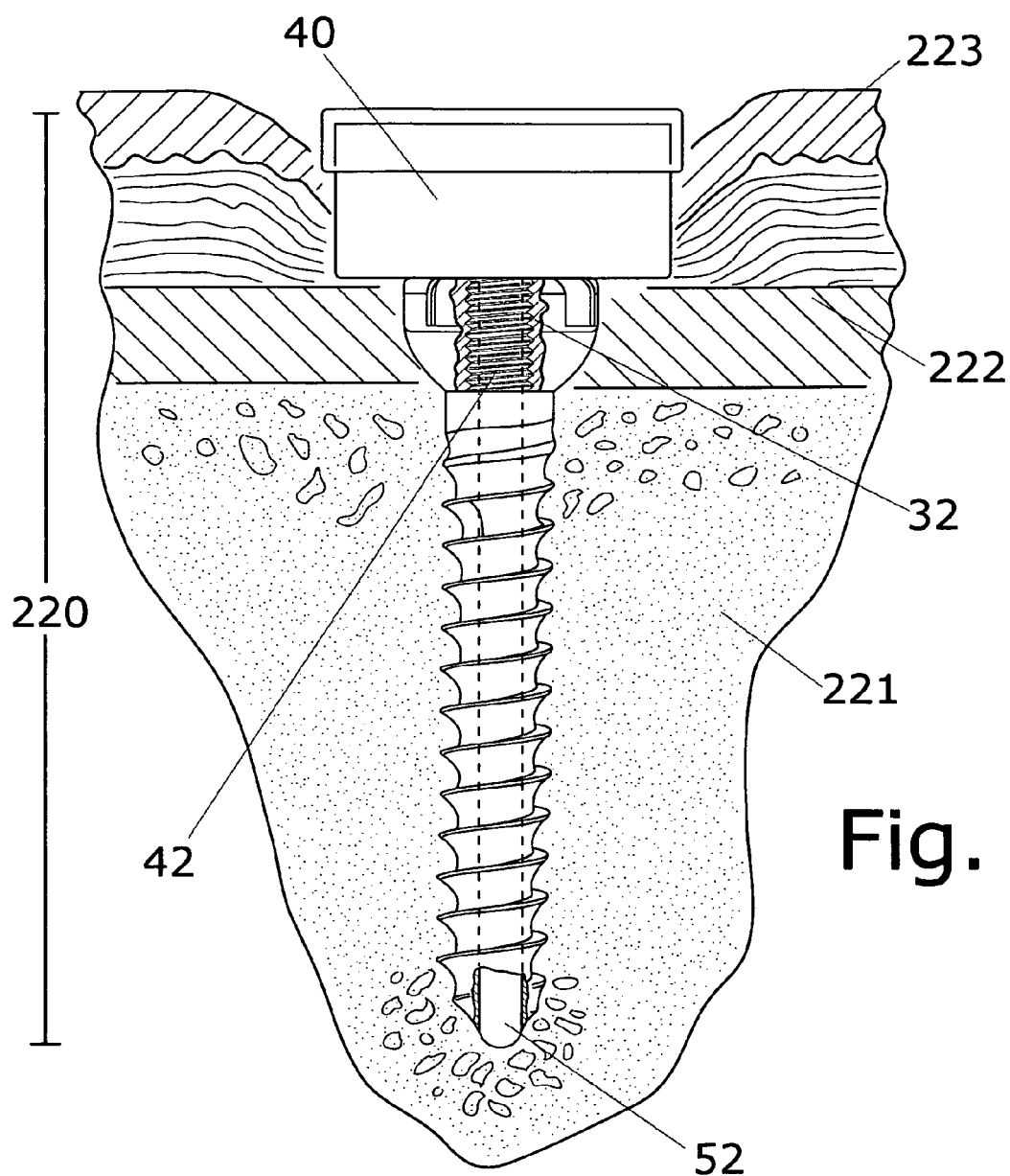
FIG. 1 is a partial cross sectional view showing the interiorly threaded dental screw and bone growth stimulator of the present invention implanted in the mucosa and mandible of a subject.
Figure 2:
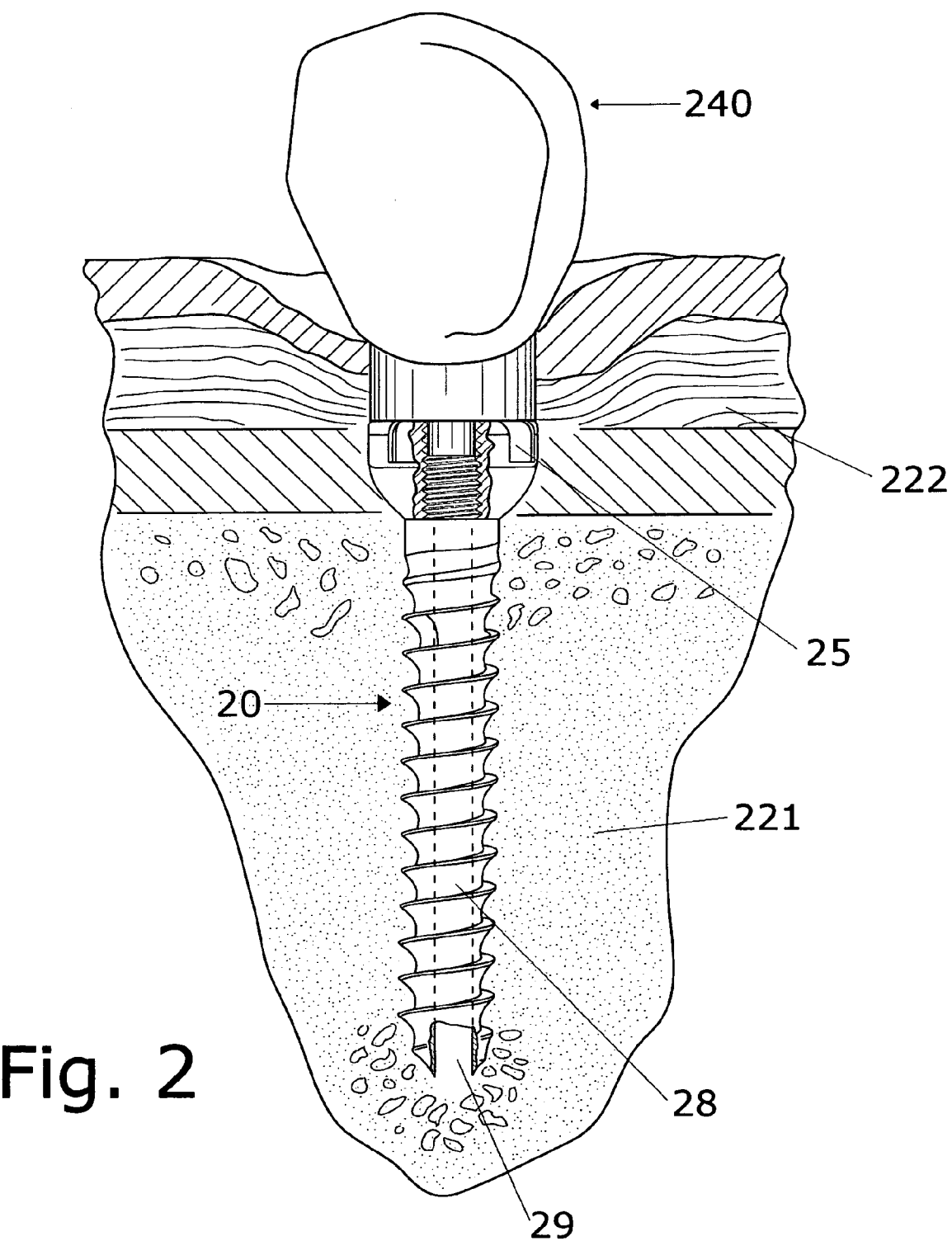
FIG. 2 is a partial cross section showing the interiorly threaded dental screw of FIG. 1 above with a prosthetic tooth in lieu of a bone growth stimulator.
Figure 6:
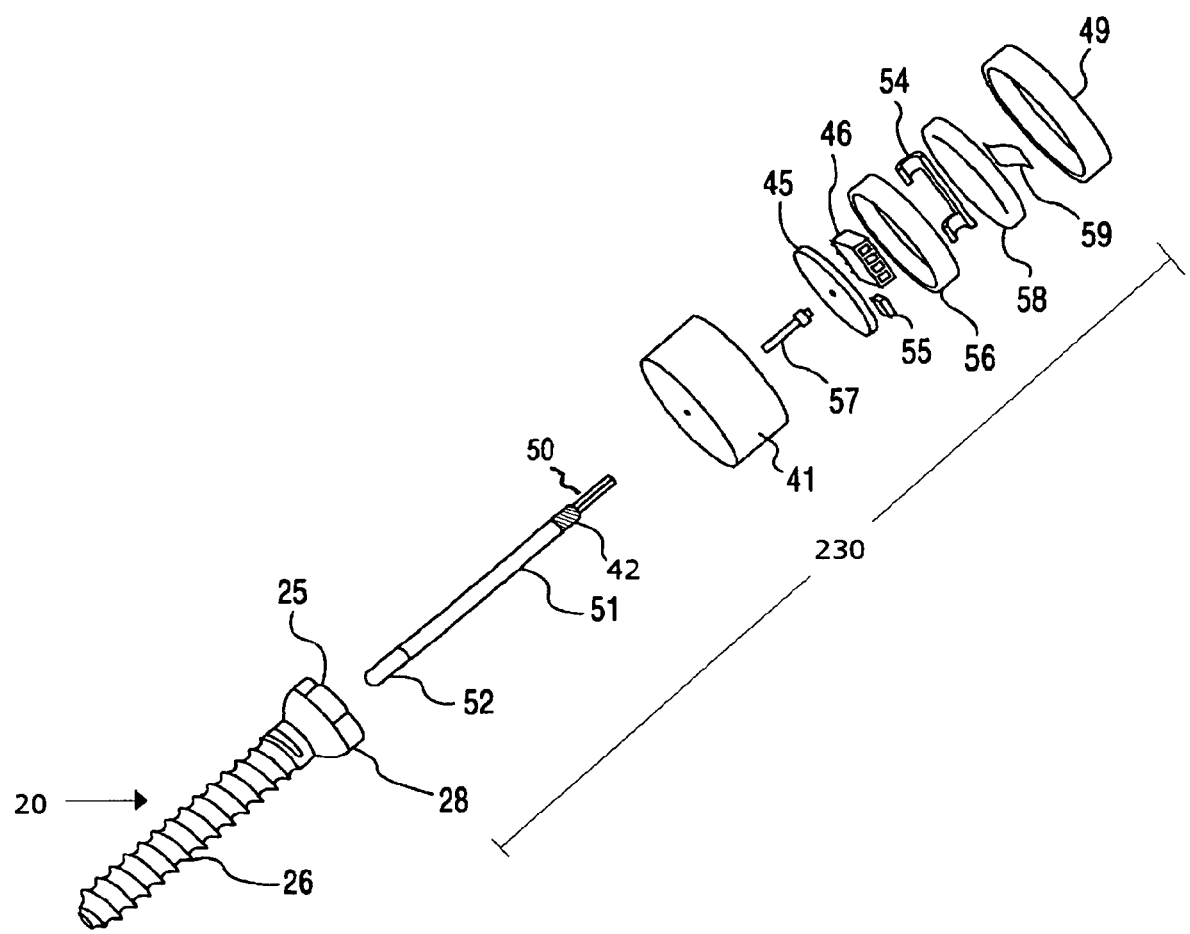
FIG. 6 is an exploded perspective view of the bone growth stimulator and interiorly threaded dental screw of the present invention.

The preferred embodiments and best modes of the invention are shown in FIGS. 1 through 8. While the invention is described in connection with certain preferred embodiments, it is not intended that the present invention be so limited. On the contrary, it is intended to cover all alternatives, modifications, and equivalent arrangements as may be included within the spirit and scope of the invention as defined by the appended claims.

The electrical dental screw implant 220 of the present invention generally comprises a cannulated threaded screw 20 and bone growth stimulator apparatus 230. After bone healing has been completed, including osteoinduction and osteointegration, the bone growth stimulator 230 (shown in FIG. 4) is replaced with a permanent prosthetic tooth 240 (shown in FIG. 5), or in an alternative embodiment, bosses 250 (shown in FIG. 9) by which bridgework 260 can be affixed.

The cannulated interiorly threaded dental screw 20 is preferably manufactured out of a non-electrically conductive, biocompatible material such as the non-bioabsorbable polymer PEEK (Polyether-ketone) or other appropriate material such as ceramic, PSU (polysulphone), PEKK (Polyether-ketone-ketone), or compositions of the same or any of a wide variety of suitable thermoplastics including other polyether ketone copolymers which are commercially available. Because the screw is insulated (nonconductive material or conductive material with nonconductive material to the tip, the current flows around the screw from the insert to the tip of the insert and does not actually flow through the screw which prevents short circuiting of current. This construction allows for a larger electrical field area than that of other electrical stimulation devices.

Alternatively, where a limited electrical field is desired, the cannulated interiorly threaded dental screw 20 can be manufactured out of conductive material such as stainless steel, titanium, titanium alloys or other conductive metal or allograft cortical bone with an inner insulated sleeve which is inserted through the screw lumen.

The interiorly threaded dental screw 20 is preferably constructed of non conductive material as previously described with a head 22 defining torque receiving means in the nature of cutouts 25 which may be four or more in number and a threaded shank 26 extending therefrom. The shank 26 defines a through going lumen or bore 28 with aperture 29 at its distal end which is centrally axially located within the shank 26 and has external threads 30 formed along at least a portion of the shank. The head 22 also defines a through going chamber 32 at the proximal end of the lumen 28 which is threaded to receive a complimentarily threaded portion of a stem 42/242 of the bone growth stimulator 230 or a prosthetic tooth 240.

Figure 7:
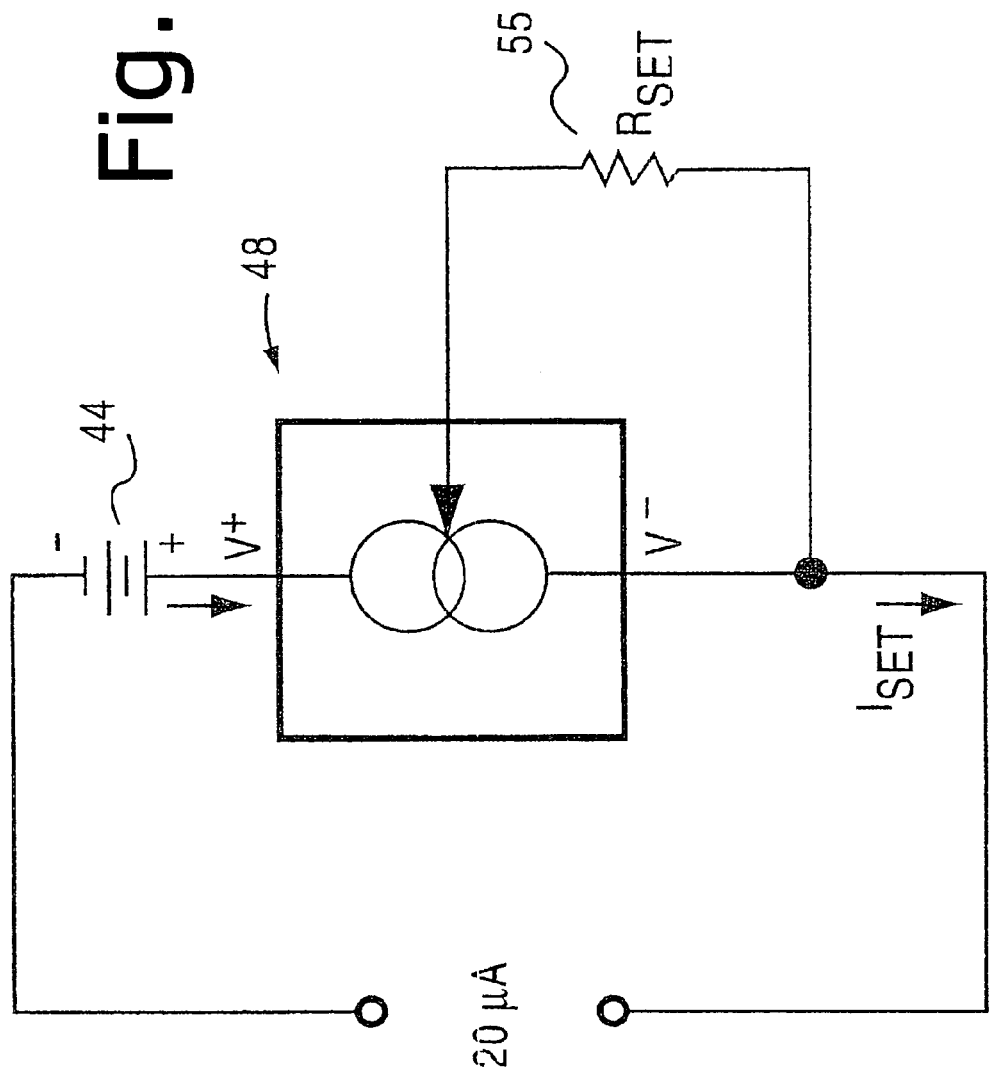
FIG. 7 is a schematic depiction of electrical operation of the bone growth stimulator.

The bone growth stimulator 230 includes a casing 40 formed at a proximal end which is preferably cylindrically shaped and hermetically sealed. Alternatively, the upper surface of casing 40 may be formed to approximate the appearance of a tooth. The casing 40 is formed with a cylindrical housing 41 and a cap 49 which is press mounted over the housing 41. Mounted in the housing 41 is an integrated circuit board 45 and a battery 44 which is electrically connected to a chip 46 which has a circuit 48 as shown in FIG. 7. The battery 44 is held in place by battery clip 54. A sealing ring 56 and sealing top member 58 are held in place by leaf spring 59 when the cap 49 is mounted over housing 41. The circuit board 45 provides a constant current source via connector member 57 to a cathode lead wire 50 encased in an insulating tube 51 extending distally from the casing 40 and circumferentially about stem 42. In use, the lead wire and insulating tube 51 are positioned through the lumen 28 of the shank 26 of the cannulated interiorly threaded dental screw 20 such that the electrically conductive tip 52 of the cathode extends from the shank 26 through aperture 29 and the casing 40 acts as an anode. The bone growth stimulator 230 produces a current ranging between about 5 µA and about 50 µA with the preferred range being between about 5 µA and about 20 µA and a most preferred value of about 20 µA. If desired as previously discussed, the casing 40 can be additionally be provided with a temperature sensor 70, a pressure sensor 72, a pH sensor 74, a global positioning sensor 76 or a microorganism sensor 78 which are housed in the casing chamber. Rechargeable lithium batteries are an alternative way to power the bioimplantable microsystem wherein the battery 44 is inductively charged thereby eliminating the necessity for battery replacement.

As shown in FIG. 5, the prosthetic tooth 240 includes a base 243 and centrally located threaded prosthetic tooth stem 242 extending normally there from having threads complimentary to those in the chamber 32 of the head 22 of the interiorly threaded dental screw 20. A conventional simulated tooth 241 is mounted to the base 243 adjacent the surface opposing the threaded prosthetic tooth stem 242.

The circuit diagram shown in FIG. 7 shows a representative current of 20 µA which can be modified as desired by changing the resistor 55 in the circuit. An RFID tag 80 can be mounted in the casing 40 allowing easy identification of the implant outside of the patient's body with the additional benefit that it can be used to power the implant 220.

Alternatively the present invention can use a signal conditioning circuit for a remotely rechargeable system. A rechargeable lithium ion battery powers this circuit. The desired out put, then goes directly to the electrodes. A second rechargeable lithium ion battery may be included to serve as a back up and in this embodiment a lithium ion charging chip is included which is connected to the integrated circuit through a logic interface. The two batteries would work in tandem thus when one battery powers the integrated circuit, the other battery is being recharged and vice versa providing uninterruptible output thereby. The integrated circuit optionally can use a series of charge pumps or transistors to achieve the required boost in voltage. This alternate integrated circuit uses voltage detector circuits to detect battery voltages and includes a voltage regulator, pulse generator circuits, logic circuits and requisite switches.

In use, the oral surgeon typically emplaces the cannulated interiorly threaded dental screw 20 through the mucosa (i.e., gums) 222 of the mouth and into the existing opening in the patient's mandible 221 left after extraction of the diseased tooth (not shown). In a preferred embodiment, a tool is used whereby the cutouts 25 in the head 22 of the interiorly threaded dental screw 20 are engaged in order to apply torque thereto, thus advancing the screw 20 into the patient. Thereafter, the bone growth stimulator 230 is threaded into the lumen 28 of the interiorly threaded dental screw 20 such that the threaded portion of its stem 42 engages the complimentary threads in the interiorly threaded dental screw 20. The bone growth stimulator 230 is preferably threaded such that its casing 40 is at or below the surface 223 of the mucosa 222 whereby the surrounding dentition will tend to protect the implant 220 and its surgical site from damage. Thereafter, the device provides an electrical current to facilitate healing including osteoinduction of new bone and osteointegration of the interiorly threaded dental screw 20 into the mandible 221. Once healing is complete, the prosthetic tooth 240 is threaded in in lieu of the bone growth stimulator 230 to thereby effect a permanent repair of the damaged tooth.

The stem 42 of the device extends through the entire length of the cannulated interiorly threaded dental screw 20 and the tip 52 forming the cathode extends into the cancellous tissues of the mandible such that the current field is facilitated along the entire length of the screw 20 thereby distributing current for osteogenesis.

Figure 8:
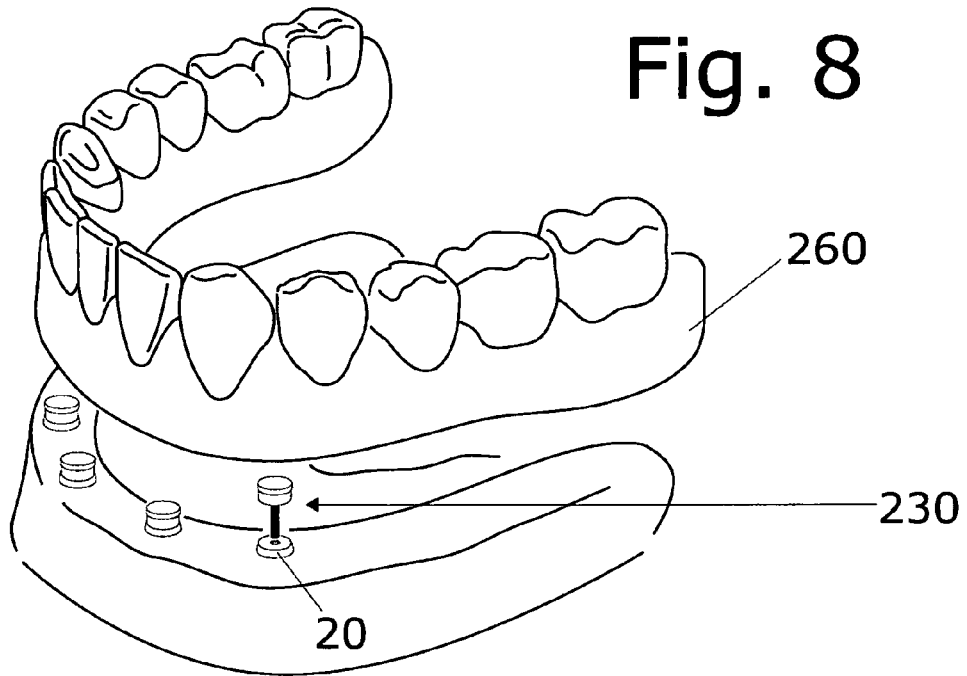
FIG. 8 is a perspective view of an alternate embodiment of the present invention immediately after implantation; and, FIG. 9 is a perspective view of the alternate embodiment shown in FIG. 8 after bone healing has been completed.
Figure 9:
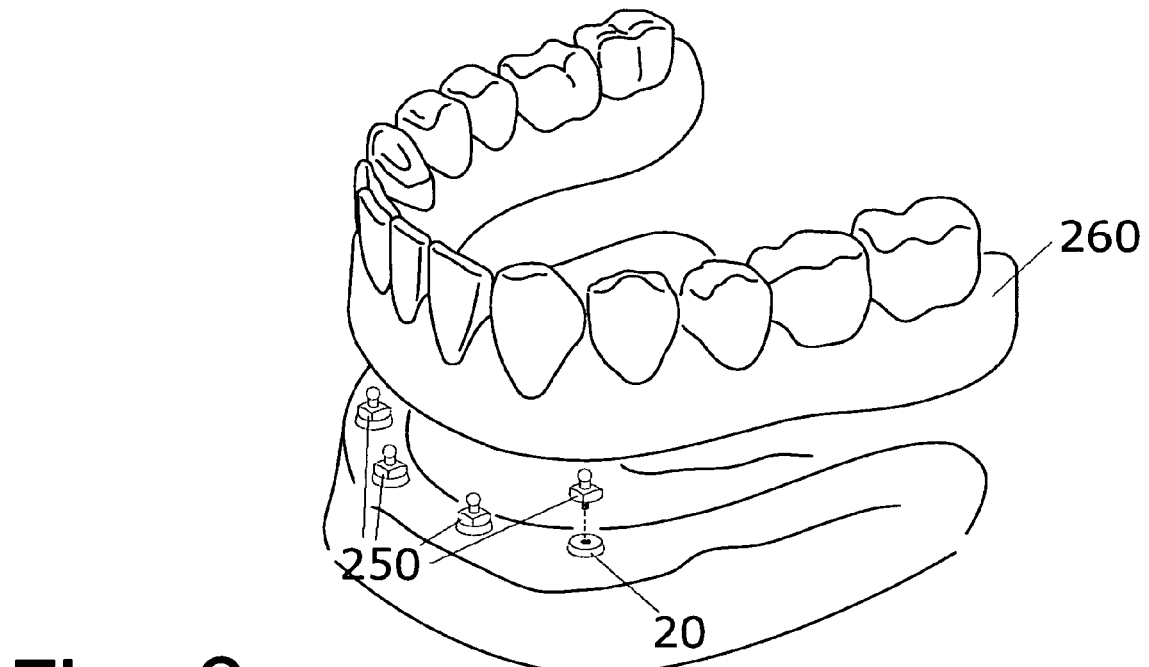

In an alternative embodiment as shown in FIGS. 8 and 9, where multiple adjacent teeth must be replaced, threaded bosses 250 may be used in lieu of a prosthetic tooth 240. Here, a plurality of interiorly threaded dental screws 20 are implanted and at the completion of healing, bosses are attached thereto in order to support bridgework.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present invention as defined by the following claims:

What I claim is:

1. An osteogenesis device for providing electrical stimulation in bone comprising: a dental screw implant member constructed of a nonconductive material defining a longitudinal through going lumen and defining torque receiving means, a hermetically sealed bone growth stimulator device removably mounted to said implant member, said device comprising a casing and stem member mounted to said casing and extending away from said casing, a battery mounted in said casing, said battery generating a constant current source in the range of about 1 $\mu A$ to about 50 $\mu A$, and circuit means connecting said battery to a lead wire, said lead wire being electrically connected to said stem member, said stem member projecting beyond a distal end of said screw implant member with a tip of said stem member serving as a cathode.

2. The device of claim 1 wherein said dental screw implant is constructed from material chosen from the group consisting of ceramic, non-conductive thermoplastic, PEEK (Poly-ether-ketone), PSU (polysulphone), PEKK (Polyether-ketone-ketone), and polyether-co-ketone.

3. The device of claim 1 wherein said bone growth stimulator stem extending there from is threaded and is removably mounted on said dental screw implant member.

4. The device of claim 1 wherein said battery generates a constant current source in the range of about 5 $\mu A$ to about 20 $\mu A$.

5. The device of claim 1 including a radio frequency identification chip embedded therein to relay information to an external receiver and/or be used to power the circuit of the implant.

6. The device of claim 1 wherein said battery is externally rechargeable.

7. An electrical dental screw implant comprising: an implant screw with a head and shank of nonconductive material, said head further comprising torque receiving means., said shank being formed with external screw threads and defining an internal threaded bore running the length of the shank, a hermetically sealed bone growth stimulator removably mounted to said implant screw, said stimulator comprising a housing at a proximal end, a rechargeable battery mounted in said housing, electrical communication means connecting said battery to a lead wire extending distally from said battery and engaging an externally threaded stem means mounted to said housing and extending distally there from, said externally threaded stem means comprising an outer insulated tube section and an inner electrically conductive tubular member being adapted to be mounted in said implant screw shank bore and extending through said shank bore outside the distal tip of said implant screw with the tip of said conductive tubular member forming a cathode.

8. An electrical dental screw implant as claimed in claim 7 wherein said implant screw is constructed from material chosen from the group consisting of ceramic, non-conductive thermoplastic, PEEK (Poly-ether-ketone), PSU (polysulphone), PEKK (Polyether-ketone-ketone), and polyether-co-ketone.

9. An electrical dental screw implant as claimed in claim 7 wherein said battery generates a constant current source in the range of about 1 $\mu A$ to about 50 $\mu A$.

10. An electrical dental screw implant as claimed in claim 7 further including a radio frequency identification tag mounted in said casing to relay information to an external receiver and/or be used to power the circuit of the implant.

11. An electrical dental screw implant as claimed in claim 7 further including a backup battery.

12. An electrical dental screw implant as claimed in claim 7 further including a temperature sensor mounted in said casing.

13. An electrical dental screw implant as claimed in claim 7 further including a pressure sensor mounted in said casing.

14. An electrical dental screw implant as claimed in claim 7 further including a pH sensor mounted in said casing.

15. An electrical dental screw implant as claimed in claim 7 further including a microorganism sensor mounted in said casing.

16. An electrical dental screw implant as claimed in claim 10 further including a global positioning sensor mounted in said casing.

17. An electrical dental screw implant comprising: an implant screw with a head and shank of nonconductive material, said head defining torque receiving means, said shank being formed with external screw threads and defining an internal bore running the length of the shank, a hermetically sealed bone growth stimulator removably mounted to said implant screw, said stimulator further including a housing and rechargeable battery therein at a proximal end, electrical communication means connecting said battery to a lead wire extending distally from said battery, stem means including an electrically conductive tip mounted to said housing and extending distally there from, said stem means being adapted to be mounted to said implant screw shank, said stem means extending outside the distal tip of said implant screw forming a cathode so that a constant current in a range of about 5 μA to about 20 μA is generated around said stem means when the implant screw and stimulator are implanted in the bone of a patient and a prosthesis adapted to be mounted to said implant screw.

18. An electrical dental screw implant as claimed in claim 17 wherein said prosthesis is chosen from the group consisting of a prosthetic tooth and a prosthetic boss adapted to mount dental bridgework.

19. An electrical dental screw implant as claimed in claim 17 including a radio frequency identification chip embedded therein to relay information to an external receiver and/or be used to power the circuit of the implant.

* * * * *